United States Patent [19]

Watanabe et al.

[11] 4,011,274
[45] Mar. 8, 1977

[54] 1,1-DIPHENYL ETHANE PROCESS

[75] Inventors: Masaaki Watanabe; Masao Hasegawa; Jiroe Yamada; Kouichi Kobayashi, all of Tokyo, Japan

[73] Assignee: Asahi-Dow Limited, Tokyo, Japan

[22] Filed: May 19, 1976

[21] Appl. No.: 687,768

Related U.S. Application Data

[62] Division of Ser. No. 423,986, Dec. 12, 1973, abandoned.

[30] Foreign Application Priority Data

Jan. 13, 1973   Japan .............................. 48-6735

[52] U.S. Cl. ..................... 260/668 C; 260/171 R
[51] Int. Cl.² ..................................... C07C 15/10
[58] Field of Search ..................... 260/668 C, 671

[56] References Cited

UNITED STATES PATENTS 2,282,327   5/1942   Dreisbach ................... 260/668 C
2,308,415   1/1943   Dreisbach ................... 260/668 C
3,674,884   7/1972   Moritani ..................... 260/668 C

OTHER PUBLICATIONS

André Jung et al., Memoires Presents a La Societe' Chimique, No. 102, pp. 587–596, 1964.

*Primary Examiner*—Veronica O'Keefe
*Attorney, Agent, or Firm*—Flynn & Frishauf

[57] ABSTRACT

A novel heating medium comprising 1,1-diphenyl ethane is provided for use in heating processes. Said heating medium has good thermal stability, a high boiling point and a low melting point. It is applicable over a wide range of temperatures and easily degradable by microorganisms. The oily substances, by-produced in the step of separating ethyl benzene from polyalkyl benzenes in production of ethyl benzene from the reaction between benzene and ethylene, may be available for preparation of said heating medium.

4 Claims, No Drawings

1,1-DIPHENYL ETHANE PROCESS

RELATED APPLICATIONS

This application is a division of application Ser. No. 423,986, filed Dec. 12, 1973 now abandoned.

This invention relates to a process for producing a novel heating medium which is excellent in thermal stability and to a process for producing said medium. More particularly, this invention relates to a heating medium having good thermal stability, a high boiling point and a low melting point, which is applicable over a wide range of temperatures and easily degradable by microorganisms.

Heating of substances or bodies up to a temperature around 300° C. is frequently required in many industries, including the chemical industry. A great variety of heating media have been used for that purpose. Among these, good heating media are those which are highly stable to heat or water, capable of maintaining liquid state over a wide range of temperatures, not corrosive against equipment, low in toxicity to living bodies and degradable by microorganisms. Heretofore, such heating media as an eutectic mixture of diphenyl ether and diphenyl, alkyl naphthalene hydrocarbons, hydrogenated triphenyl hydrocarbons, polycyclic hydrocarbon mixtures, polychloro-biphenyl, etc., have been known. However, an eutectic mixture of diphenyl ether and diphenyl has a high melting point and freezes at low temperatures to cause troubles when stopping or starting up operations. Alkyl naphthalene hydrocarbons and polycyclic hydrocarbon mixtures are inferior in thermal stability and liable to deteriorate. Polychloro-biphenyl is decomposed by water or heat with generation of corrosive substances and therefore it can be used only under limited conditions. In addition, it is harmful to living bodies. Thus, none of the heating media of the prior art are possessed of sufficient properties required for a heating medium.

The object of the present invention is to provide a process for producing a heating medium, which has overcome the above drawbacks of the conventional heating media and can be applicable in various uses.

Another object of the present invention is to provide a cheap heating medium.

It has now been found that 1,1-diphenyl ethane is the most suitable heating medium. The heating medium according to the present invention is more preferable as 1,1-diphenyl ethane is purer. In other words, 100 percent pure compound is the best. However, the compound need not always be pure. 1,1-Diphenyl ethane may contain, for example, aromatic or other hydrocarbons having higher or lower boiling points than 1,1-diphenyl ethane in amounts up to 55% by weight, preferably 40% by weight, most preferably 20% by weight for those having lower boiling points and up to 35% by weight, preferably 15% by weight, most preferably 5% by weight for those having higher boiling points, the percentages being based on the total weight. If the content of the components having lower boiling points is more than 55% by weight, and if the content of the components having higher boiling points is more than 35% by weight, thermal stability is worsened.

The heating medium of the present invention may be prepared according to various methods. For example, benzene and styrene or benzene and acetaldehyde are allowed to react at a comparatively low temperature, using as a catalyst hydrogen chloride, aluminum chloride or concentrated sulfuric acid, followed by neutralization, and the reaction mixture is separated by fractional distillation to obtain the product. However, the practically suitable method for producing the heating medium of the present invention comprises rectifying oily substances by-produced as by-products in the production of ethyl benzene from the reaction between benzene and ethylene, e.g., oily substances obtained as the tower bottom liquid in a distillation tower of polyalkyl benzene, and recovering portions containing 1,1-diphenyl ethane, for example, fractions at 75° to 90° C./1 mm. Hg.

The tower bottom liquid in a distillation tower of polyalkyl benzene is a mixture of hydrocarbons having various boiling points and contains, other than 1,1-diphenyl ethane, triethyl benzene, tetraethyl benzene, pentaethyl benzene, hexaethyl benzene, ethyl-substituted 1,1-diphenyl ethane, 1-cyclohexyl-1-phenyl ethane, and the like. Said liquid, however, had heretofore found no specific uses but for fuels, although U.S. Pat. No. 2,308,415 teaches re-use of benzene and ethyl benzene obtained by decomposition in the presence of catalyst of 1,1-diphenyl ethane by-produced as by-products in the production of ethyl benzene from ethylene and benzene.

The present inventors have purified the aforesaid tower bottom liquid, obtained fractions containing 1,1-diphenyl ethane and found that they are extremely excellent heating media as mentioned above. The starting material cost is very low because the heating media are produced from the tower bottom liquids which had heretofore been evaluated merely as fuels. In addition, production cost is further cut because the residue after removal of the heating medium is still available as fuels.

Although distillation may be carried out under either normal, reduced or increased pressure, distillation under reduced pressure is generally advantageous in industrial applications. Either batch-feed or continuous-feed distillation may be practiced. The number of theoretical plates of the distillation tower is determined according to the extent of purification to be attained. Industrially, however, from 10 to about 100 plates are suitable. The type of the distillation tower is tray type or packed column type, which is suitably selected according to the amount of product to be obtained. The number of distillation towers should be at least two in case of continuous-feed operation, namely, one for removal of high boiling point distillates and the other for removal of low boiling point distillates.

The heating medium of the present invention has the following advantages over known heating media. Namely, as mentioned above, the eutectic mixture of diphenyl ether and diphenyl is excellent in thermal stability, but its melting point is +12° C. and its boiling point is also slightly lower, i.e., 257° C. Whereas, the heating medium of the present invention containing 1,1-diphenyl ethane has a melting point of −30° C. and cannot be frozen under normal operational conditions even if it is allowed to stand without heating in winter. Furthermore, it has a boiling point as high as about 270° C. to the advantage of relatively low vapor pressure at higher temperatures. An alkyl naphthalene heating medium is inferior in thermal stability and the highest use temperature is about 320° C., while the heating medium of the present invention is superior in thermal stability and can be used at about 30° C. higher than 320° C. Although polycyclic hydrocarbon mixtures have a very low freezing point, they are inferior in thermal stability and regeneration of once deteriorated medium by means of distillation or other methods is generally difficult, because it is a mixture of many compounds, which is an economical disadvantage. On the contrary, the heating medium of the present invention is not only useful at the highest temperature, but also greatly advantageous in easy regeneration by means of distillation and re-use of the deteriorated medium after prolonged operations. Polychloro-biphenyl, in addition to poor biodegradability and strong residual toxicity, has drawbacks in thermal decomposition and corrosive property, while the heating medium of the present invention is superior in biodegradability as well as in thermal stability and corrosive property.

The well-balanced excellent properties possessed by the heating medium of the present invention as described above may be construed to be due to the chemical structure of 1,1-diphenyl ethane constituting said medium. That is, because said compound is a hydrocarbon, it is more easily available than organic compounds containing fluorine, silicon, etc., and it has no corrosive property as it contains no chlorine. Biodegradability is excellent because it contains no nucleus-substituted chlorine. In order to improve the heat-resistant property of hydrocarbons, it is preferred that hydrocarbons should be constituted of many aromatic nuclei with a lesser amount of alkyl groups, while such hydrocarbons have such higher freezing points that they are inconvenient for practical use. The contradictory requirement that such excellent thermal stability should be maintained without increasing freezing point seems to be accomplished in 1,1-diphenyl ethane by its asymmetric molecular structure and absence of superfluous alkyl groups on the aromatic nucleus. Furthermore, since the main component is a single substance, regeneration by means of distillation is also very easy.

The heating media according to the present invention may be used for heating in the state of high temperature vapor by effectively utilizing the latent heat of vaporization similarly as in case of conventional heating media. It is also possible to use the heating media of the present invention in the state of a high temperature liquid under increased pressure, if desired. The mode of use, which is more advantageous, is suitably selected depending on the positions and arrangements of high temperature and low temperature sides by heat transfer, the temperature controlling system, the extent of requirement for uniformity of heating, etc. The present heating media may also be used in the form of a mixture with other heating media at various ratios, so long as it may be practiced without departure from the object of the present invention. For example, a mixture of 1,1-diphenyl ethane of the present invention with 72% by weight of the eutectic mixture of diphenyl ether and diphenyl (the percentage is based on the total weight) has a melting point of 0° C., which is much lower than the melting point of said eutectic mixture (12° C.), and so it is very convenient for practical use. It is a problem of cost what the other medium is and how much the other medium is.

The present invention will now be further explained by referring to the following Examples, which are shown only for illustrative purposes.

EXAMPLE 1

Into a test distillation apparatus of a coil packed column (number of theoretical plates: about 40), 20 mm. in diameter and 2000 mm. in height, was charged 2000 ml. of a tower bottom liquid taken out of a distillation tower for distilling polyalkyl benzenes in the process for manufacturing ethyl benzene from benzene and ethylene. Distillation was commenced under vacuum of 1 mm. Hg. absolute at a reflux ratio of 5. After about 5 hours, steady state was reached and distillate was obtained at the rate of 3 to 10 ml./hour. As the distillate at the distillation temperatures from 75° C. to 90° C., 500 ml. of slightly yellow liquid was obtained as a sum in fractions (a), (b), (c), (d) and (e), 100 ml. per each fraction. Separately, by the use of a conventional distillation flask, the above tower bottom liquid was subjected to a single distillation to obtain the samples (f) and (g). These samples were analyzed by means of gas chromatography, mass spectrography and infra-red analysis to give the results as shown in Table 1. All of these samples had freezing points of −30° C. or lower.

Table 1

| Sample | (% by weight) | | |
|---|---|---|---|
| | Higher boiling point components | Lower boiling point components | 1,1-diphenyl ethane |
| (a) | 0 | 35.2 | 64.8 |
| (b) | 0 | 18.4 | 81.6 |
| (c) | 0 | 5.1 | 94.9 |
| (d) | 3.2 | 4.8 | 92.0 |
| (e) | 15 | 1.5 | 83.5 |
| (f) | 30.4 | 23.8 | 45.8 |
| (g) | 15.0 | 53.2 | 31.8 |

EXAMPLE 2

This Example is shown for the purpose of illustrating comparison of thermal stability.

Eighty ml. of the Sample (c) were charged into an autoclave of stainless steel having 100 ml. capacity. The autoclave was sealed, and heated to 386° C., whereby the rate of increase of pressure was observed. Thermal stability is indicated by the rate of increase of pressure, because the lower the thermal stability is, the more low molecular weight substances are produced as the result of pyrolysis to show higher pressure. The initial pressure was 6.8 Kg./cm.$^2$ and thereafter linearly increased as the lapse of time at the rate of 0.18 kg./cm.$^2$/hour. For comparison, similar tests by means of an autoclave were conducted for commercially available heating media to be used in gaseous phase, namely Neo-SK oil 240 of alkyl naphthalene, KSK oil 260 of polycyclic hydrocarbon (each produced by Soken Kagaku Co., Ltd.) and Therm-S 200 (produced by Shinnihon Seitetsu Kagaku Kogyo Co., Ltd.). The results were that the initial pressures were 10.4, 7.5 and 7.6 Kg./cm.$^2$, respectively, and the rates of increase of pressure 0.28, 0.37 and 0.68 Kg./cm.$^2$/hour, respectively. The Sample (c) was found to be an improved heating medium having excellent thermal stability as indicated by the small rate of pressure increase as well as by the low initial pressure.

EXAMPLE 3

Thermal stability tests by means of an autoclave were conducted in the same manner as in Example 2 for the Samples (a) through (g) of Example 1 and, for comparative purposes, for commercially available heating media, namely, NKH 1,000 (produced by Nihon Sekiyu Kagaku Co., Ltd.) and Mobil Thermo 600 of mineral oil (produced by Mobil Oil Co.). The results are as shown in Table 2. It is shown that the Samples (a) through (e) have excellent thermal stabilities comparable to those of the expensive commercially available heating media. It is also shown that the Samples (f) and (g) are superior in thermal stability to the heating medium of mineral oil, although they are considerably inferior as compared with the Samples (a) through (e).

data in Table 2 show that this substance belongs to the class inferior in thermal stability as a single component heating medium, when compared with other commercially available heating media.

Table 2

| Heating Medium | Initial pressure (Kg/cm$^2$) | Rate of increase of pressure (Kg/cm$^2$/hr) | Components (Note) | | |
|---|---|---|---|---|---|
| Example 1: | | | | | |
| Sample (a) | 7.1 | 0.36 | DPE 64.8%; | LBP | 35.2% |
| Sample (b) | 6.9 | 0.28 | DPE 81.6%; | LBP | 18.4% |
| Sample (c) | 6.8 | 0.18 | DPE 94.9%; | LBP | 5.1% |
| Sample (d) | 6.5 | 0.28 | DPE 92%; HBP 3.2% | LBP | 4.8%; |
| Sample (e) | 6.3 | 0.57 | DPE 83.5%; HBP 15% | LBP | 1.5%; |
| Sample (f) | 7.0 | 1.08 | DPE 45.8%; HBP 30.4% | LBP | 23.8%; |
| Sample (g) | 8.8 | 1.09 | DPE 31.8%; HBP 15% | LBP | 53.2%; |
| Example 4 | 5.2 | 0.13 | DPE | | |
| Neo-SK 240 | 10.4 | 0.28 | Methyl naphthalene | | |
| Therm-S 200 | 7.6 | 0.68 | Dimethyl naphthalene | | |
| Comparative example | 4.8 | 0.45 | 1,1-tolyl phenyl ethane | | |
| KSK 260 | 7.5 | 0.37 | Polycyclic hydrocarbon | | |
| Santotherm 66 | 0.7 | 0.18 | Hydrogenated triphenyl | | |
| NKH 1000 | 3.4 | 0.28 | | | |
| Mobil Therm 600 | 0.6 | 2.4 | Mineral oil | | |

(Note):
DPE: 1,1-diphenyl ethane
LBP: lower boiling point components
HBP: higher boiling point components.

EXAMPLE 4

Into 2500 g. of benzene were added separately 200 g. of styrene and 200 g. of 93% concentrated sulfuric acid dropwise over two hours with stirring, while maintaining the temperature at 30° C. After the stirring was further continued for one hour, benzene was separated from the acid and, after washing with water, neutralized with caustic soda. This was distilled under reduced pressure to obtain 100 g. of a fraction having a boiling point of 148° C. under 15 mm. Hg. abs. This fraction was identified by gas chromatography to be 1,1-diphenyl ethane. Autoclave tests similar to Example 2 were conducted for this synthetic substance and, for comparative purposes, for the heating medium of hydrogenated triphenyl series, namely, Santotherm 66 (produced by Mitsubishi-Monsanto Kasei Co., Ltd.). The results are set forth in Table 2, which clearly shows that the heating medium of the present invention has excellent thermal stability.

As a comparative example, thermal stability of 1,1-tolyl phenyl ethane was measured. As a result, thermal stability of this compound is extremely inferior as compared with that of 1,1-diphenyl ethane. It is entirely unexpected that a slight difference in molecular structure can bring about so much difference in thermal stability between two substances. Namely, 1,1-tolyl phenyl ethane was obtained according to the same procedure as in Example 4 except that toluene was used in place of benzene. The purity of the product was 99.8%. In spite of such high purity, when an autoclave test was conducted for this substance in a manner analogous to Example 2, the rate of increase of pressure was indicated to be as high as 0.45 Kg./cm.$^2$/hour. The

EXAMPLE 5

A mixture comprising equal amounts of a commercially available eutectic mixture of diphenyl ether and diphenyl, namely, Dowtherm A (produced by The Dow Chemical Co., U.S.A.) and the Sample (d) of Example 1 were subjected to the thermal stability test similarly as in Example 2. The rate of increase of pressure was measured to be 0.15 Kg./cm.$^2$/hour. Said mixture had a freezing point of −10° C. or lower and handling thereof at cold times is by far easier than that of Dowtherm A.

EXAMPLE 6

This Example is presented to show that a heating medium of the present invention is biologically degradable.

Into 1000 ml. of pure water were dissolved 0.03 g. of the Sample (d) of Example 1, 3 g. of ammonium chloride, 1 g. of potassium dihydrogen phosphate, 0.25 g. of magnesium sulfate heptahydrate, 0.25 g. of potassium chloride, 0.002 g. of ferrous sulfate heptahydrate and 0.3 g. of yeast extract to prepare a culture liquid. By the use of this culture liquid, acclimatization of the sludge taken from the drainage outside the factory manufacturing ethyl benzene was carried out for 72 hours, which was repeated twice. To 150 ml. of a newly prepared culture liquid were added 15 ml. of the above acclimatized liquid and culturing was carried out under shaking. The percentages of the residual heating medium after 72 hours and 120 hours were 5% and 1%, respectively, to indicate that rapid biological degradation occurred.

What is claimed is:

1. A process for obtaining 1,1-diphenyl ethane, which comprises
   reacting ethylene and benzene to form ethyl benzene and high boiling by-products, and fractionally distilling said higher boiling by-products and recovering a fraction consisting essentially of 1,1-diphenyl ethane.

2. The process of claim 1, wherein a fraction containing 1,1-diphenyl ethane and up to 55 percent by weight of hydrocarbons having a lower boiling point than 1,1-diphenyl ethane is so recovered.

3. The process of claim 1, wherein a fraction containing 1,1-diphenyl ethane and up to 35 percent by weight of hydrocarbons having a higher boiling point than 1,1-diphenyl ethane is so recovered.

4. The process of claim 1, wherein a fraction containing 1,1-diphenyl ethane, up to 55 percent by weight of hydrocarbons having a lower boiling point than 1,1-diphenyl ethane, and up to 35 percent by weight of hydrocarbons having a higher boiling point than 1,1-diphenyl ethane, is so recovered.

* * * * *